US011041706B2

United States Patent
Kimura

(10) Patent No.: US 11,041,706 B2
(45) Date of Patent: Jun. 22, 2021

(54) FEED MECHANISM AND MEASURING DEVICE INCLUDING THE SAME

(71) Applicant: Mitutoyo Corporation, Kanagawa (JP)

(72) Inventor: Kazuhiko Kimura, Tochigi (JP)

(73) Assignee: Mitutoyo Corporation, Kanagawa (JP)

( * ) Notice: Subject to any disclaimer, the term of this patent is extended or adjusted under 35 U.S.C. 154(b) by 169 days.

(21) Appl. No.: 16/279,963

(22) Filed: Feb. 19, 2019

(65) Prior Publication Data

US 2019/0257635 A1  Aug. 22, 2019

(30) Foreign Application Priority Data

Feb. 19, 2018 (JP) .............................. JP2018-027146

(51) Int. Cl.
| | |
|---|---|
| *G01B 3/20* | (2006.01) |
| *G01B 21/02* | (2006.01) |
| *G01B 5/00* | (2006.01) |
| *F16H 25/12* | (2006.01) |
| *G01B 5/06* | (2006.01) |
| *A61B 5/107* | (2006.01) |

(52) U.S. Cl.
CPC .............. *G01B 3/20* (2013.01); *A61B 5/1072* (2013.01); *F16H 25/12* (2013.01); *G01B 5/0002* (2013.01); *G01B 5/061* (2013.01); *G01B 21/02* (2013.01)

(58) Field of Classification Search
CPC .......... G01B 3/20; G01B 5/061; G01B 21/02; G01B 5/0002; G01B 21/18; G01B 21/08; G01B 21/00; A61B 5/1072; F16H 25/12; F16H 19/04; B23Q 5/34
See application file for complete search history.

(56) References Cited

U.S. PATENT DOCUMENTS

| | | | | | |
|---|---|---|---|---|---|
| 5,477,621 | A | * | 12/1995 | Koizumi | G01B 3/004 29/592.1 |
| 6,446,351 | B1 | * | 9/2002 | Zhang | G01B 5/061 33/556 |
| 6,522,040 | B2 | * | 2/2003 | You | H02K 7/1853 290/1 A |

(Continued)

FOREIGN PATENT DOCUMENTS

| | | |
|---|---|---|
| JP | 4377156 | 9/2009 |
| JP | 2015-165233 | 9/2015 |

*Primary Examiner* — Nimeshkumar D Patel
*Assistant Examiner* — Tania Courson
(74) *Attorney, Agent, or Firm* — Oblon, McClelland, Maier & Neustadt, L.L.P.

(57) ABSTRACT

Described is a feed mechanism for a slider which is convenient to use with good durability and low costs by eliminating a rack-and-pinion method. The feed mechanism allows the slider to be fed and moved along a longitudinal main scale. The feed mechanism includes a driving gear that is a gear train pivotally supported by the slider, a driven roller that meshes with the driving gear and rotates by rotation of the driving gear, and an arm that includes a cup portion capable of receiving the driven roller on a distal end. The arm includes the cup portion capable of receiving the driven roller on the distal end and is pivotally supported by the slider on a base end. The cup portion in a state of receiving the driven roller is biased toward the main scale by a pin plunger. Accordingly, the driven roller is kept abutted against the main scale.

13 Claims, 6 Drawing Sheets

(56) References Cited

U.S. PATENT DOCUMENTS

| | | | | |
|---|---|---|---|---|
| 7,210,239 B2* | 5/2007 | Otsubo | ............... | G01B 5/0009 33/1 M |
| 7,624,512 B2* | 12/2009 | Zhang | .................... | G01B 5/213 33/553 |
| 8,065,812 B2* | 11/2011 | Zhang | ..................... | G01B 3/22 33/533 |
| 8,931,185 B2* | 1/2015 | Emtman | ............... | G01B 3/002 33/784 |
| 9,021,715 B2* | 5/2015 | Emtman | ................. | G01B 3/30 33/784 |
| 9,441,715 B2* | 9/2016 | Onodera | ............. | G01B 5/0004 |
| 2003/0047009 A1* | 3/2003 | Webb | .................... | G01B 3/205 33/784 |
| 2007/0068027 A1* | 3/2007 | Suzuki | .................. | G01B 3/205 33/784 |
| 2011/0036184 A1* | 2/2011 | Zhang | ..................... | G01N 3/20 73/862.621 |
| 2014/0150272 A1* | 6/2014 | Emtman | ................. | G01B 3/18 33/558.04 |

* cited by examiner

FEED MECHANISM AND MEASURING DEVICE INCLUDING THE SAME

TECHNICAL FIELD

The present disclosure relates to a feed mechanism for a slider, for example, to a feed mechanism for lifting and lowering a slider of a height gauge along a post.

BACKGROUND ART

There is a measuring device including a slider movable along a post, for example, a height gauge. The measuring device measures a size of a measuring object based on a movement amount of the slider (Patent Document 1: JP 4377156 B). In order to move the slider, a rack (spur gear) is provided on a side surface of the post so that the slider is moved by mesh between the rack and a pinion pivotally supported on the slider.

CITATION LIST

Patent Literature

Patent Document 1: JP 4377156 B
Patent Document 2: JP 2015-165233 A

SUMMARY OF INVENTION

Technical Problem

Good mesh between the rack and the pinion is indispensable for moving the slider accurately with good operability.

However, there are processing difficulties and costs in cutting teeth accurately on a long rack (spur gear train) for covering a measurement length. Further, a tooth surface may be damaged when fine dust, such as a metal shaving, is caught between the rack and the pinion, and positioning may become unstable.

A thumb roller applied to, for example, a caliper has been previously used. A feed mechanism is also known in which a user moves a slider along a main scale by rotating the thumb roller while pushing the thumb roller with a thumb (for example, Patent Document 2: JP 2015-165233 A).

Although these methods do not suffer from the problems associated with rack and pinion, it may nevertheless be difficult to rotate the thumb roller while pushing it with the thumb as the slider of the height gauge is also heavy. There is also a problem in usability in terms of measurement efficiency when using the thumb roller alone to move from an end to an end of a measurement stroke.

The same problem is not limited to the height gauge but is a problem common to measuring devices that measure a size of a measuring object based on a relative movement amount between a main scale and a slider.

An object of the disclosure is to provide a feed mechanism for a slider which is convenient to use with good durability and low costs by eliminating the rack-and-pinion method.

Solution to Problem

The described embodiments provide a feed mechanism that feeds and moves a slider movable relatively along a longitudinal main scale of the slider, the feed mechanism including:

a driving gear that is a gear train pivotally supported by the slider;

a driven roller configured to mesh with the driving gear directly or indirectly and to rotate by rotation of the driving gear, the driven roller being kept abutted against the main scale;

an arm that is pivotally supported by the slider on a base end, the arm including a cup portion capable of receiving the driven roller on a distal end; and a biaser configured to bias the cup portion, which is in a state of receiving the driven roller, toward the main scale.

According to an embodiment, the driven roller preferably includes:

a driven gear that is a gear train meshing with the driving gear directly or indirectly;

a clamping disk that is provided coaxially with the driven gear, the clamping disk being paired with the driven gear to clamp the main scale; and a coupling shaft configured to coaxially couple the driven gear and the clamping disk.

According to an embodiment, a diameter of the clamping disk is preferably smaller than a diameter of the driven gear.

According to a third embodiment, the arm is preferably pivotally supported so as to be coaxial with a rotation axis of the driving gear.

Further, a measuring device of the invention preferably includes the feed mechanism described above.

DESCRIPTION OF EMBODIMENTS

Figure 1:
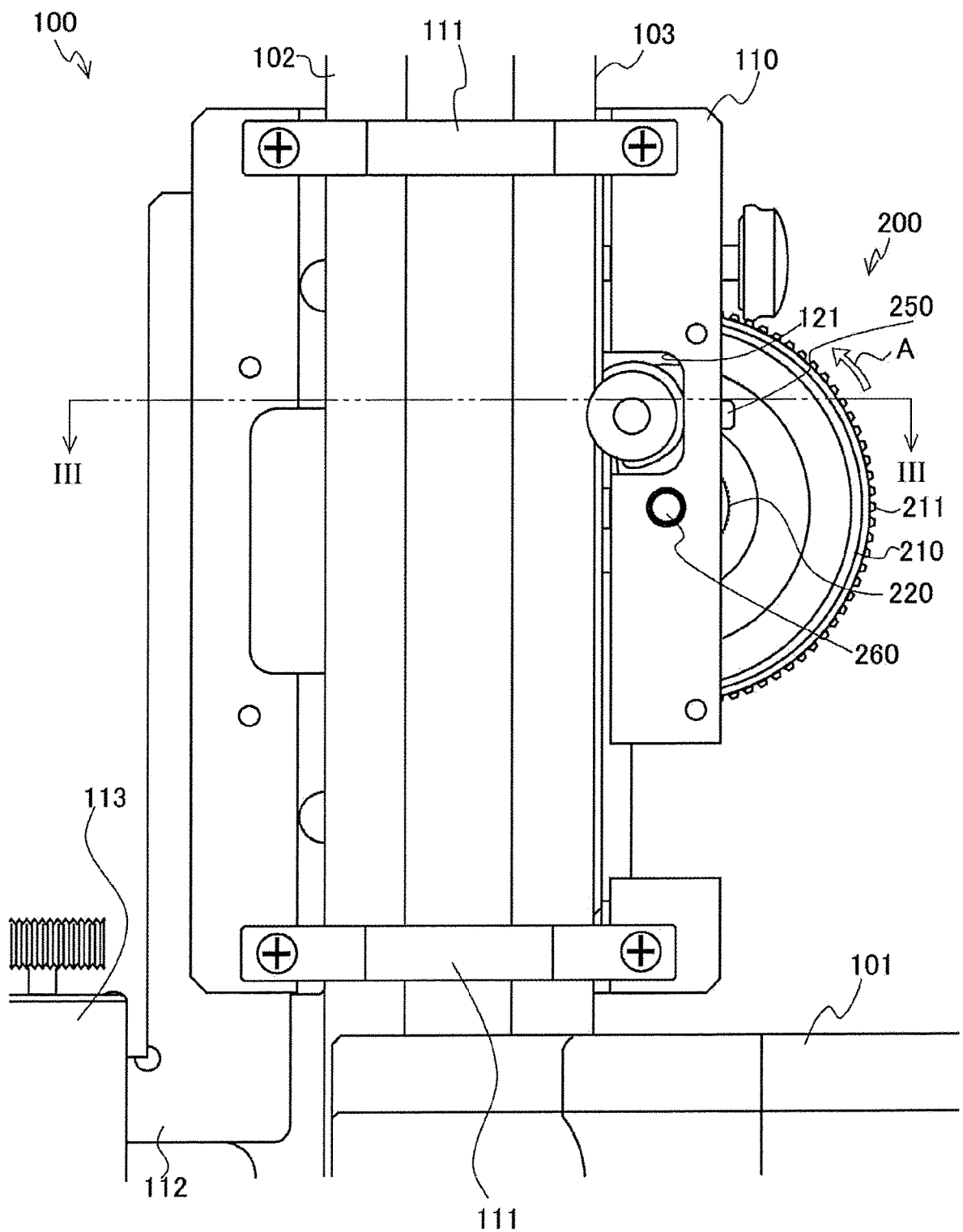
FIG. 1 is an enlarged view of a slider in a front view of a height gauge.

An embodiment will now be described with reference to the drawings and the reference numerals appended to the elements illustrated in the drawings.

First Embodiment

A first embodiment will now be described.
The first embodiment will be described with reference to FIGS. 1 to 5.

FIG. 1 is an enlarged view of a slider 110 in a front view of a height gauge 100 described in the present embodiment.

Figure 2:
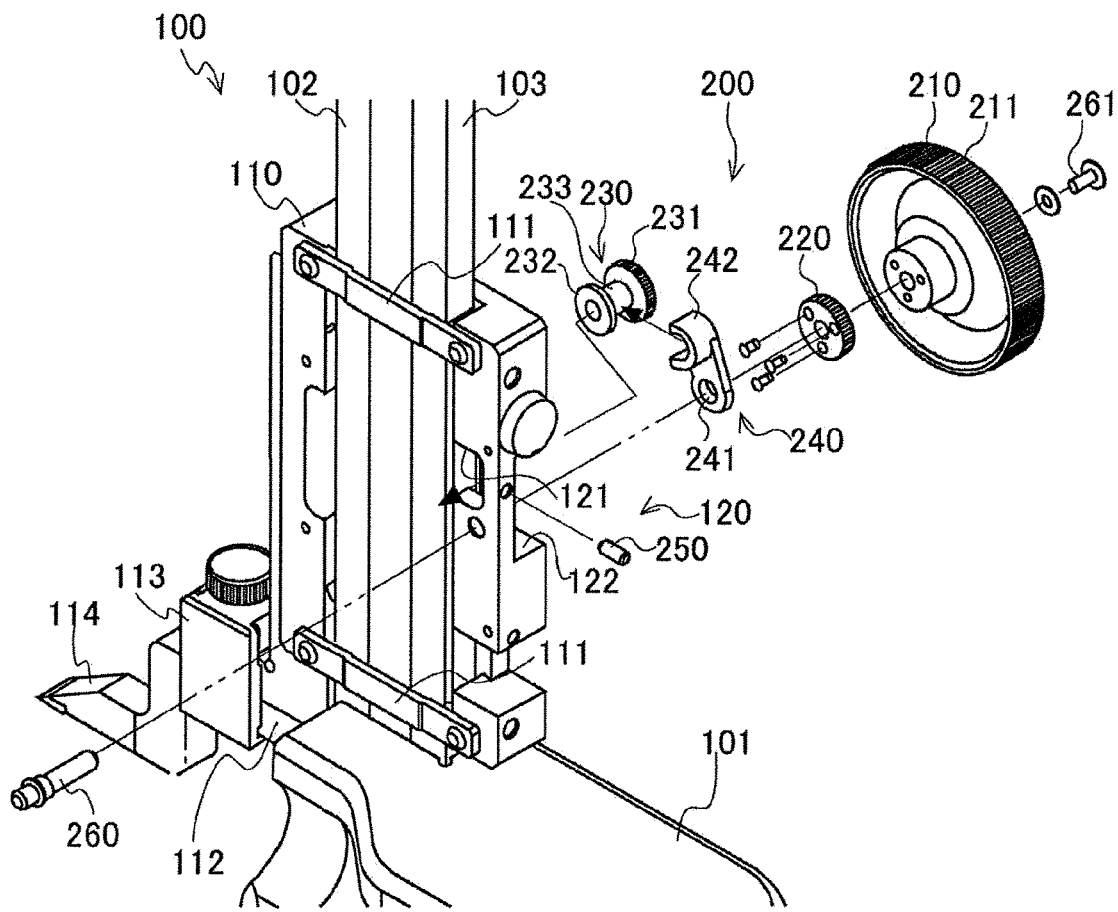
FIG. 2 is an exploded perspective view of a feed mechanism.

FIG. 2 is an exploded perspective view for easy understanding of a configuration of a feed mechanism 200.

The height gauge 100 includes a base 101, a post 102 serving as a main scale erected on the base 101, a slider 110 movable up and down along the post 102, and a feed mechanism 200 that moves the slider 110.

The post 102 is made of, for example, metal, and has a rectangular cross section.

In the present embodiment, a side surface 103 of the post 102 is finished to be as straight and flat as possible, so as to be a reference guide surface of slider movement. It should be noted that, a rack is, although conventionally provided on the side surface 103 of the post 102, not required in the present embodiment.

The slider 110 has a substantially U-shaped cross section and is attached to the post 102 so as to hold the post 102 inside.

In FIGS. 1 and 2, the slider 110 is attached to the post 102 from a back surface side of the post 102. On a front surface side of the post 102, horizontal bars 111 bridge the slider 110 and are screwed to an upper end and a lower end of the slider 110 respectively. Accordingly, the slider 110 is slidable in a vertical direction along the post 102 without being detached from the post 102.

To facilitate understanding of the descriptions, the left side of the drawings in FIGS. 1 and 2 will be called the "front" of the height gauge 100 and the right side will be called the "rear" of the height gauge 100.

The slider 110 is provided with a jaw 112 protruding forward at a lower end of a front side thereof. A scriber 114 is fixed to the jaw 112 via a fixing unit 113.

Electrical circuitry including a digital display, a detection head of a linear encoder, and the like is attached to a front surface side of the slider 110.

On a rear side of the slider 110, a feed mechanism attaching unit 120 is provided for the attachment of the feed mechanism 200. Although the feed mechanism 200 is disposed to the feed mechanism attaching unit 120, a structure of the feed mechanism attaching unit 120 will be described below in conjunction with a configuration of the feed mechanism 200.

The feed mechanism 200 includes a handle 210, a driving gear 220, a driven roller 230, an arm 240, and a pin plunger 250.

The handle 210 is of a short cylindrical shape having such a radius that is just right to be held by a hand of a person, on a side surface of which knurls 211 are provided.

The driving gear 220 is a so-called gear train and is screwed to a back side of the handle 210 to be coaxial therewith. That is, the handle 210 and the driving gear 220 rotate integrally.

The driven roller 230 includes a driven gear 231, a clamping disk 232 coaxial with the driven gear 231, the clamping disk 232 being paired with the driven gear 231 to clamp a side surface of the post 102, and a coupling shaft 233 coaxially coupling the driven gear 231 and the clamping disk 232.

The driven roller 230 appears to be an H shape when viewed in a plane passing through the center of the coupling shaft 233.

Figure 3:
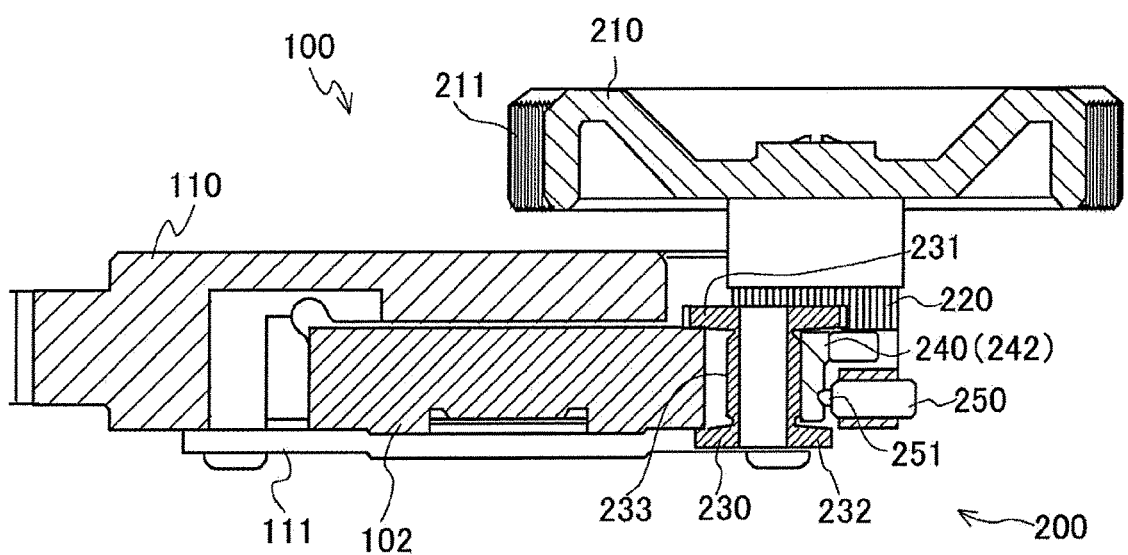
FIG. 3 is a cross-sectional view taken from the line II-II in FIG. 1.

FIG. 3 is a cross-sectional view taken from the line II-II in FIG. 1.

In FIG. 3, the driven roller 230 has a substantially H-shaped cross section.

However, surfaces of the driven gear 231 and the clamping disk 232 opposing each other are slightly tapered, so that an interval between the driven gear 231 and the clamping disk 232 increases slightly as separated from the coupling shaft 233.

The driven gear 231 is a gear train and is formed with teeth on an outer surface to mesh with the teeth of the driving gear 220 appropriately. The clamping disk 232 only needs to be flat without teeth on an outer surface.

A radius of the clamping disk 232 is slightly smaller than a radius of the driven gear 231.

A certain size is required for the radius of the driven gear 231 as it is necessary to provide teeth on the driven gear 231.

Meanwhile, by pairing with the driven gear 231, the clamping disk 232 only needs to have a radius enough for the side surface 103 of the post 102 to be clamped, and there may be no machining allowance (cutting allowance) for teeth and the like.

In a case where teeth are cut in the driven gear 231 after the driven roller 230 is integrally molded, there is an advantage that the teeth are easily processed only on the driven gear 231 without the clamping disk 232 interfering with strokes of a blade (bite) since the driven gear 231 and the clamping disk 232 have different radii. The driven roller 230 may be molded by high density compression molding. In this case, material costs are reduced with a small clamping disk 232.

The coupling shaft 233 couples the driven gear 231 and the clamping disk 232 coaxially.

The coupling shaft 233 is hollow in the cross-sectional view in FIG. 3, and it may also be solid.

As illustrated in FIG. 3, the coupling shaft 233 only needs to have such a length that the taper defined by the opposing surfaces of the driven gear 231 and the clamping disk 232 contacts and clamps the post 102 when the driven roller 230 is pressed against the side surface of the post 102.

The arm 240 is a flat rod as a whole and includes a shaft hole 241 on a base end and a cup portion 242 like a half pipe on a front end.

Figure 4:
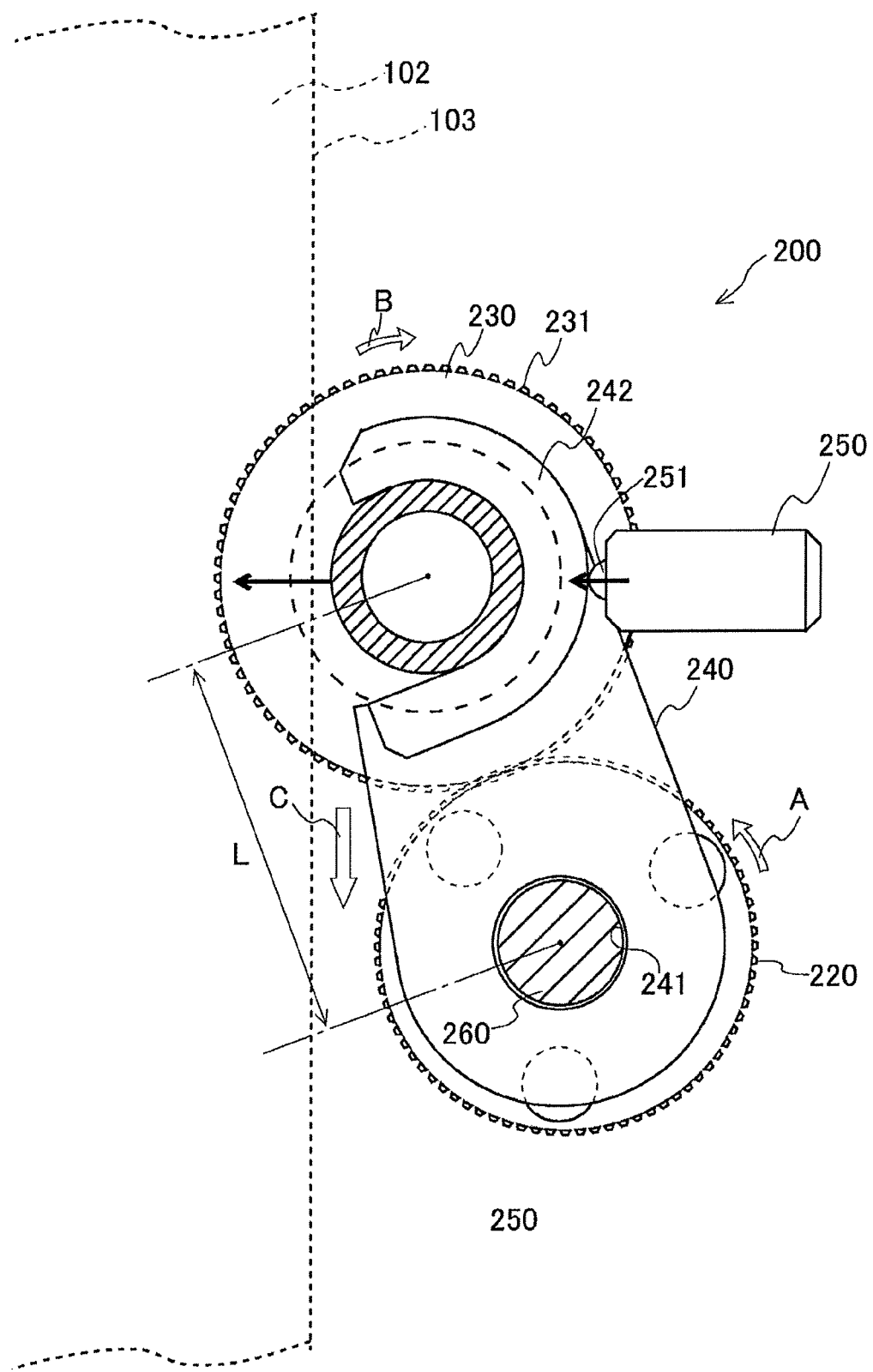
FIG. 4 is an enlarged view of a main part of the feed mechanism.

FIG. 4 is an enlarged view of a main part of the feed mechanism 200.

A distance L between a center of the shaft hole 241 of the arm 240 and the center of the cup portion 242 is equal to a sum of a radius of the driving gear 220 and the radius of the driven gear 231.

An axis of the shaft hole 241 is parallel to an axis of the cup portion 242. A direction in which the cup portion 242 is opened in the cup portion 242 is substantially orthogonal to a longitudinal direction of the arm 240. The cup portion 242 is capable of receiving the coupling shaft 233 of the driven roller 230.

The pin plunger 250 extrudes a pin 251 at a top end with a built-in spring (not illustrated). The pin plunger 250 is fixedly attached to a hole in the side surface of the slider 110 and biases the cup portion 242 toward the post 102 to push the cup portion 242 forward from rear.

Assembling of the feed mechanism 200 and the configuration of the feed mechanism attaching unit 120 will now be described.

First, a U-shaped recess 121 is formed in a surface on a rear side of the slider 110 opposing the side surface 103 on a rear side of the post 102. The recess 121 is referred to as the driven roller housing recess 121 as it is used for receiving the driven roller 230.

The driven roller 230 is held in a gap between the side surface 103 of the post 102 and the driven roller housing recess 121.

(Details Will be Described Below)

At this time, the clamping disk 232 reaches the front surface of the slider 110, while the driven gear 231 comes to the back surface side of the slider 110.

Next, a recess 122 is formed in a back surface on the rear side of the slider 110, which is cut from the back surface toward the front surface. The recess 122 is referred to as the driving gear housing recess 122 as the arm 240 and the driving gear 220 are housed in the recess 122.

A hole is provided in the slider 110 slightly below the driven roller housing recess 121. A shaft core 260 penetrates the hole from the front surface side to the back surface side of the slider 110.

The shaft core 260 penetrates the shaft hole 241 of the arm 240, the driving gear 220, and the handle 210 successively from the front surface side and is pinned by a locking pin 261 from a side of the handle 210. In this manner, the shaft hole 241 of the arm 240, the driving gear 220, and the handle 210 will not come off. Accordingly, the shaft core 260 serves as the tilt center shaft of the arm 240, the rotation center of the driving gear 220, and the rotation center of the handle 210.

Additionally, the coupling shaft 233 of the driven roller 230 may enter the cup portion 242 of the arm 240 first, so that the driven roller 230 enters the driven roller housing recess 121 upon the attachment of the arm 240.

Finally, the pin plunger 250 is attached to the slider 110 from rear, so that the pin 251 of the pin plunger 250 extrudes the cup portion 242 of the arm 240 forward from rear.

When the feed mechanism 200 is attached to the feed mechanism attaching unit 120 of the slider 110 in this manner, the driven roller 230 abuts against the side surface 103 of the post 102 in a state of being housed in the cup portion 242 of the arm 240. The driven roller 230 is pressed against the side surface 103 of the post 102 in a state of being housed in the cup portion 242 of the arm 240 as the cup portion 242 is pushed by the pin plunger 250. Further, the driving gear 220 meshes with the driven gear 231 of the driven roller 230.

It is assumed that a user of the height gauge 100 rotates the handle 210 to adjust the height of the slider 110.

Although the user operates the handle 210 from a back surface side of the height gauge 100 and rotates the handle 210 rightward, an arrow A in the drawings appears to be leftward as the height gauge 100 is viewed from front in FIGS. 1, 2, and 4.

The driving gear 220 rotates integrally with the handle 210 (see the arrow A in FIG. 4).

Then, the driven gear 231 meshing with the driving gear 220 rotates (arrow B), and the driven roller 230 rotates accordingly.

Since the driven roller 230 is pressed against the side surface 103 of the post 102, the slider 110 moves along the post 102 together with the feed mechanism 200 (arrow C) when the driven roller 230 rotates without sliding in a state of clamping the side surface 103 of the post 102. In the present example, the slider 110 is lowered.

Figure 5:
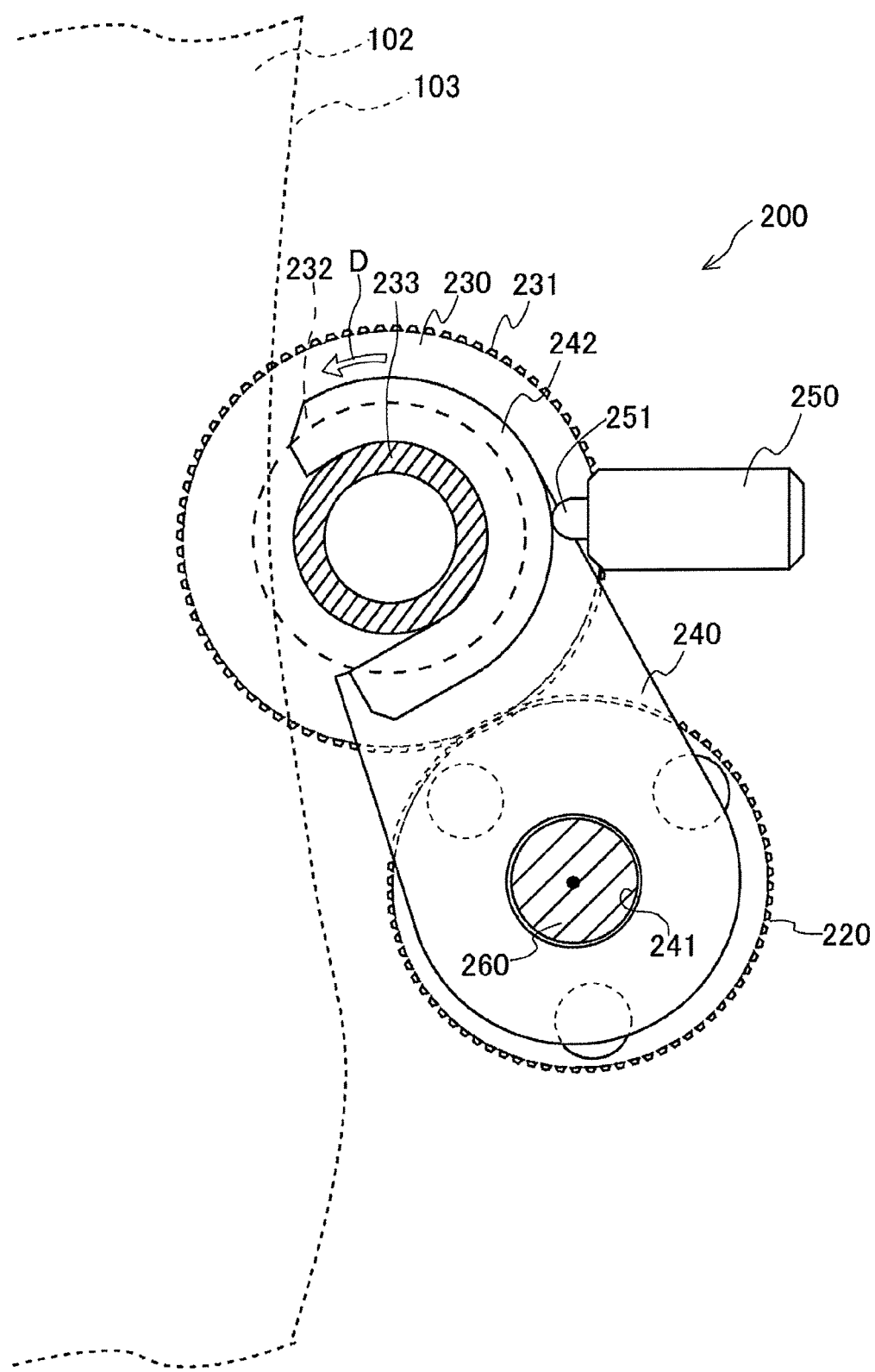
FIG. 5 is a view illustrating a case where a side surface of a post is slightly wavy.

In order to understand the operation of the feed mechanism 200 described in the present embodiment, a slightly exaggerated example is illustrated in FIG. 5. In FIG. 5, it is assumed that the side surface 103 of the post 102 is not straight but slightly wavy.

Even in this case, the driven roller 230 of the feed mechanism 200 described in the present embodiment follows the side surface 103 of the wavy post 102, and the driven roller 230 rotates without sliding in a state of clamping the side surface 103 of the post 102. A shaft (coupling shaft 233) of the driven roller 230 is not fixed to the slider 110 but is held in a state of being received by the cup portion 242 of the tiltable arm 240.

The driven roller 230 is always pressed against the side surface 103 of the post 102 while changing its position along with the tilting arm 240 as the cup portion 242 of the arm 240 is pushed by the pin plunger 250.

In FIG. 5, the arm 240 is tilted leftward (arrow D) compared to a state in FIG. 4, and the pin 251 of the pin plunger 250 protrudes further than in FIG. 4.

In this manner, the driven roller 230 rotates without sliding in a state of clamping the side surface 103 of the post 102 no matter how wavy the side surface 103 of the post 102 is.

Further, the driven gear 231 and the driving gear 220 are maintained meshing appropriately even though the driven roller 230 changes its position with the waviness of the side surface 103 of the post 102.

A distance L between the center of the shaft hole 241 of the arm 240 and the center of the cup portion 242 is equal to a sum of a radius of the driving gear 220 and the radius of the driven gear 231. Thereby, the distance between the driven gear 231 and the driving gear 220 stays constant even if the arm 240 is tilted around the shaft hole 241.

The driven gear 231 and the driving gear 220 are maintained meshing appropriately as the driven roller 230 is held by the cup portion 242. Accordingly, operability during the feed operation of the slider 110 is favorably maintained even though the finishing of the side surface 103 of the post 102 is slightly poor.

In this manner, a rack is unnecessary when the feed mechanism 200 described in the present embodiment is adopted. As it is not necessary to prepare a long rack (spur gear train) that covers a measurement length, problems caused by the rack such as manufacturing costs and damages of tooth surfaces are all eliminated. Further, a longer stroke of the height gauge 100 is also simple since the rack is unnecessary.

Modified Example 1

Some modified examples of the first embodiment will now be supplemented.

In the above embodiment, the driving gear 220 and the driven gear 231 of the driven roller 230 mesh with each other directly. However, another sequence of gear trains may also be disposed between the driving gear 220 and the driven gear 231.

In the above embodiment, the pin plunger 250 is exemplified as a biasing unit (biaser) for pushing the cup portion 242 toward the side surface 103 of the post 102. However, the invention is not limited to the pin plunger 250, and may be any member that can exert a biasing force such as a leaf spring, a coil spring, and an elastic rubber.

Further, although the cup portion 242 is pushed from rear, the same effect can be obtained when a biasing force is exerted to pull the cup portion 242 toward the support post 102.

In the above embodiment, the shaft core 260 is inserted into the shaft hole 241 of the arm 240, so that the tilt center of the arm 240 and the rotation center of the driving gear 220 are the same.

In this configuration, although there is an advantage that a meshing depth between the driven gear 231 and the driving gear 220 does not change at all, there will be no particular problem even if the distance between the driven gear 231 and the driving gear 220 is slightly changed as long as the meshing is not broken down. Therefore, the tilt center of the arm 240 may be shifted from the rotation center of the driving gear 220, and the base end of the arm 240 may be pivotally supported somewhere in the slider 110.

Second Embodiment

A second embodiment will now be described.

A basic configuration described in the second embodiment is the same as that described in the first embodiment and is an example suitable for applying a feed mechanism to a smaller meter.

Figure 6:
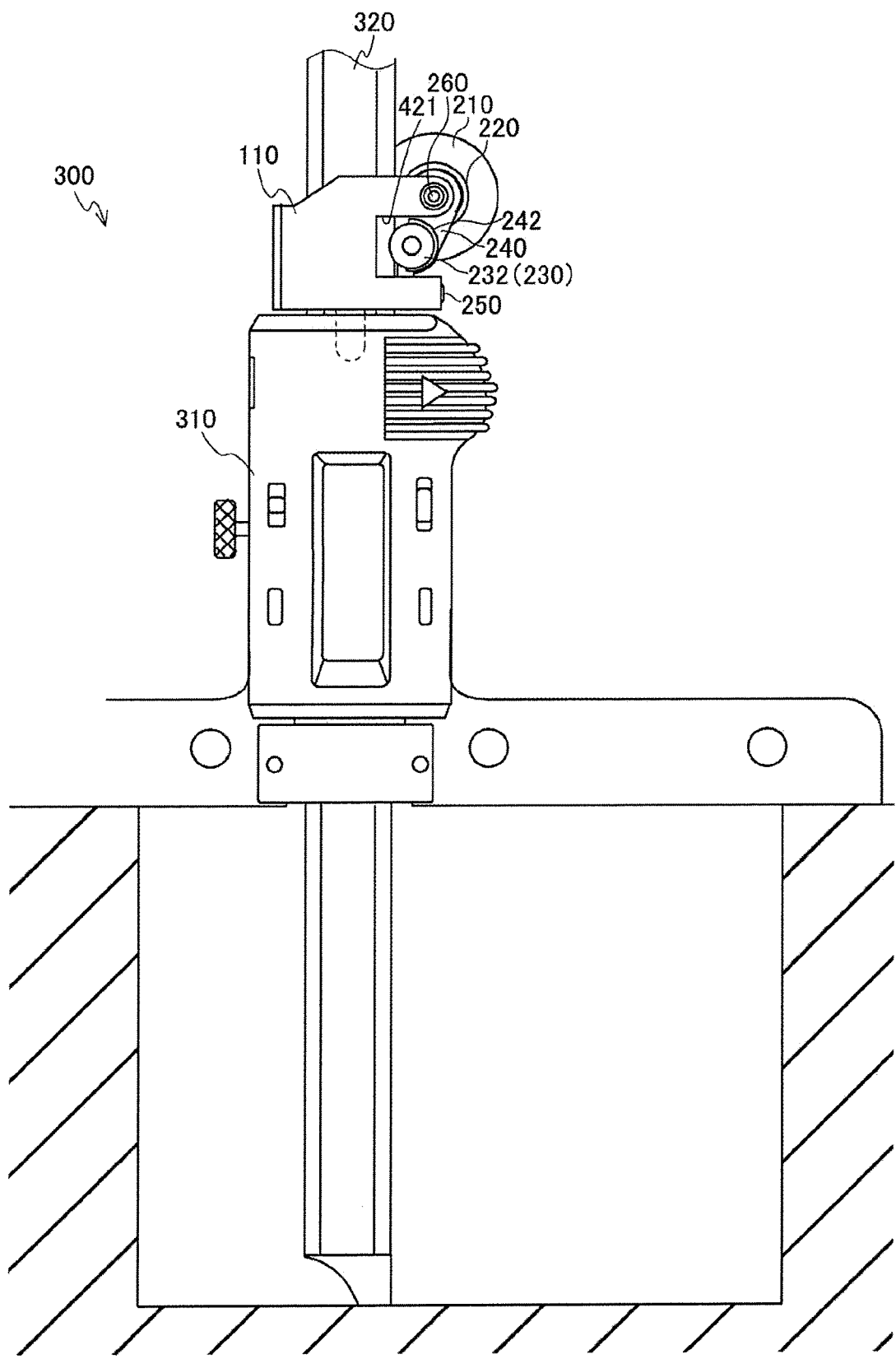
FIG. 6 is a view illustrating an example in which a feed mechanism is applied to a depth gauge.

FIG. 6 illustrates an example of a depth gauge 300. A so-called caliper may also be used although the depth gauge is illustrated here.

The depth gauge 300 allows a main scale 320 to be fed and moved relative to a detection head 310.

The feed mechanism 200 is attached to a rear end of the detection head 310.

Figure 7:
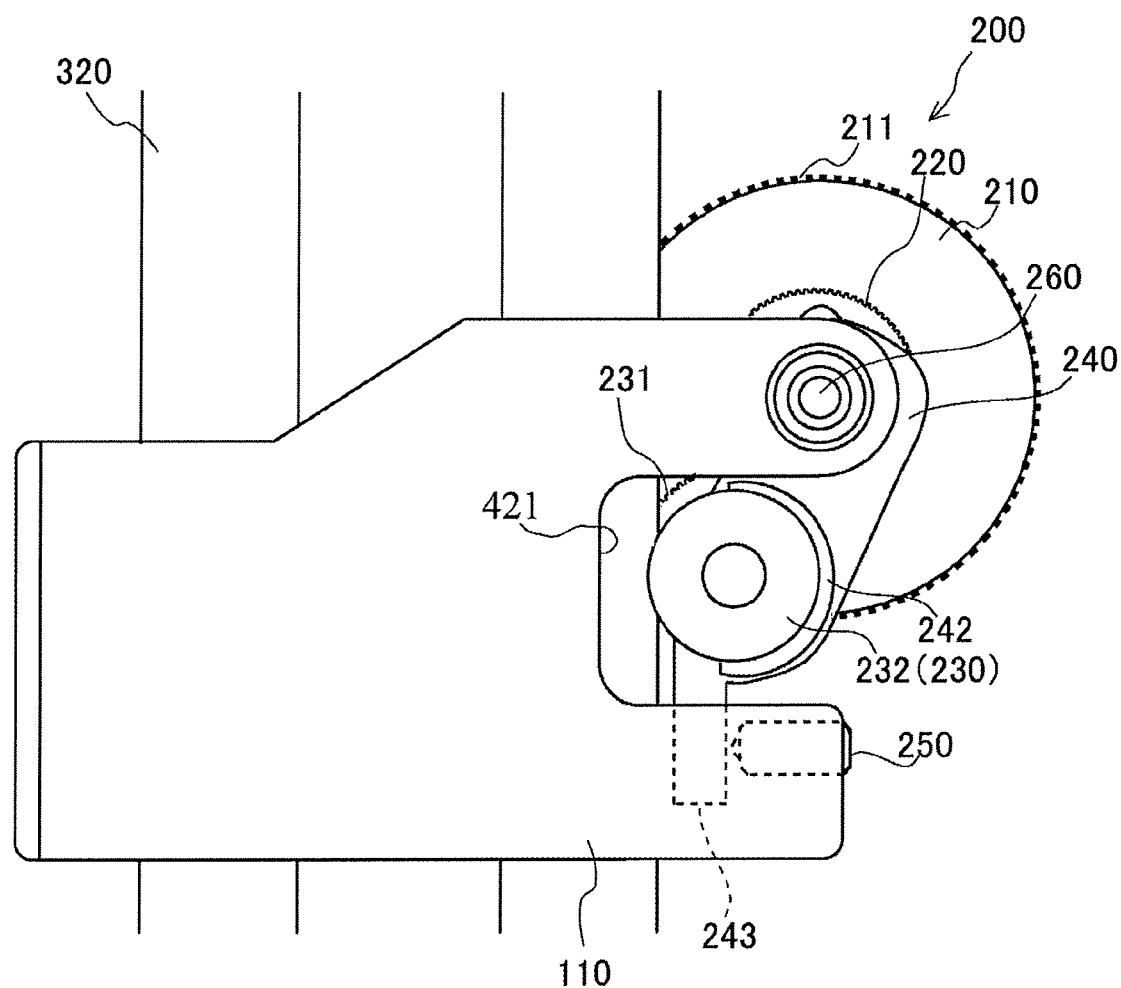
FIG. 7 is an enlarged view of the feed mechanism.

FIG. 7 illustrates an enlarged view of the feed mechanism 200. The feed mechanism described in the second embodiment is basically the same as that described in the first embodiment. Accordingly, corresponding elements are denoted by the same reference numerals, and descriptions thereof will not be repeated.

In the first embodiment, the pin plunger 250 can be attached to the driven roller 230 directly from rear as the surface of the slider 110 opposing to the side surface 103 of the post 102 is recessed in a U-shape to form the driven roller housing recess 121.

However, in this configuration, a member like the slider 110 is necessary in rear of the driven roller 230, which may result in a slightly large size of the feed mechanism 200.

In this respect, in the second embodiment, a driven roller housing recess 421 of the slider 110 is cut from a side away from the main scale 320 toward the main scale, so that there is no member of the slider 110 in rear of the driven roller 230.

In such a case, a push plate 243 extends from a front end of the arm 240, so that the arm 240 is slightly elongated. Then, the pin plunger 250 only needs to be attached to the slider 110 so as to press the push plate 243 extending in this manner.

This makes it possible to further reduce the size of the feed mechanism 200.

The disclosure is not intended to be limited to the above-described embodiments, and appropriate variations can be made thereon without departing from the essential spirit of the disclosure.

Power for rotating the driving gear may be not a force for manually turning the handle only and may also be the rotation power of a motor.

REFERENCE SIGNS LIST

100 . . . Height gauge
101 . . . Base
102 . . . Post
103 . . . Side surface of post
110 . . . Slider
111 . . . Bar
112 . . . Jaw
113 . . . Fixing unit
114 . . . Scriber
120 . . . Feed mechanism attaching unit
121 . . . Driven roller housing recess
122 . . . Driving gear housing recess
200 . . . Feed mechanism
210 . . . Handle
211 . . . Knurl
220 . . . Driving gear
230 . . . Driven roller
231 . . . Driven gear
232 . . . Clamping disk
233 . . . Coupling shaft
240 . . . Arm
241 . . . Shaft hole
242 . . . Cup portion
243 . . . Push plate
250 . . . Pin plunger
251 . . . Pin
260 . . . Shaft core
261 . . . Locking pin
300 . . . Depth gauge
310 . . . Detection head
320 . . . Main scale
421 . . . Driven roller housing recess

The invention claimed is:

1. A feed mechanism for a measurement tool that feeds and moves a slider movable relatively along a longitudinal main scale of the slider, the feed mechanism comprising:
   a driving gear that is a gear train pivotally supported by the slider;
   a driven roller that meshes with the driving gear directly or indirectly and to rotate by rotation of the driving gear, the driven roller being kept abutted against the longitudinal main scale;
   an arm that is pivotally supported by the slider on a base end, the arm including a cup portion configured to receive the driven roller on a distal end; and
   a biaser that biases the cup portion, which is in a state of receiving the driven roller, toward the main scale.

2. The feed mechanism according to claim 1, wherein the driven roller includes:
   a driven gear that is a gear train meshing with the driving gear directly or indirectly;
   a clamping disk that is provided coaxially with the driven gear; the clamping disk being paired with the driven gear to clamp the main scale; and
   a coupling shaft configured to coaxially couple the driven gear and the clamping disk.

3. The feed mechanism according to claim 2, wherein the clamping disk has a radius smaller than a radius of the driven gear.

4. The feed mechanism according to claim 3, wherein the arm is pivotally supported to be coaxial with a rotation axis of the driving gear.

5. The feed mechanism according to claim 2, wherein the arm is pivotally supported to be coaxial with a rotation axis of the driving gear.

6. The feed mechanism according to claim 1, wherein the arm is pivotally supported to be coaxial with a rotation axis of the driving gear.

7. A measuring device comprising the feed mechanism according to claim 1.

8. A feed mechanism that feeds and moves a slider movable relatively along a longitudinal main scale of the slider, the feed mechanism comprising:
   a driving gear that is a gear train pivotally supported by the slider;
   a driven roller configured to mesh with the driving gear directly or indirectly and to rotate by rotation of the driving gear, the driven roller being kept abutted against the longitudinal main scale;
   an arm that is pivotally supported by the slider on a base end, the arm including a cup portion configured to receive the driven roller on a distal end; and
   a biaser configured to bias the cup portion, which is in a state of receiving the driven roller, toward the main scale, wherein
   the driven roller includes:
   a driven gear that is a gear train meshing with the driving gear directly or indirectly;
   a clamping disk that is provided coaxially with the driven gear, the clamping disk being paired with the driven gear to clamp the main scale; and
   a coupling shaft configured to coaxially couple the driven gear and the clamping disk.

9. The feed mechanism according to claim 8, wherein the clamping disk has a radius smaller than a radius of the driven gear.

10. The feed mechanism according to claim 8, wherein the arm is pivotally supported to be coaxial with a rotation axis of the driving gear.

11. A measuring device comprising the feed mechanism according to claim 8.

12. The feed mechanism according to claim 8, wherein the arm is pivotally supported to be coaxial with a rotation axis of the driving gear.

13. The feed mechanism according to claim 9, wherein the arm is pivotally supported to be coaxial with a rotation axis of the driving gear.

* * * * *